(12) United States Patent
Bowen et al.

(10) Patent No.: US 6,313,169 B1
(45) Date of Patent: Nov. 6, 2001

(54) LUTEIN ESTERS HAVING HIGH BIOAVAILABILITY

(76) Inventors: Phyllis E. Bowen, 1919 W. Taylor St., M/C 517, Rm. 650, Chicago, IL (US) 60612; James P. Clark, 40 W. Bailey Rd., Naperville, IL (US) 60565

( * ) Notice: Subject to any disclaimer, the term of this patent is extended or adjusted under 35 U.S.C. 154(b) by 0 days.

(21) Appl. No.: 09/526,902

(22) Filed: Mar. 16, 2000

Related U.S. Application Data

(63) Continuation of application No. 09/054,346, filed on Apr. 2, 1998, now abandoned.
(60) Provisional application No. 60/042,697, filed on Apr. 4, 1997.

(51) Int. Cl.$^7$ .............................. A01N 37/02; A01N 37/06
(52) U.S. Cl. .................. 514/548; 514/532; 514/533; 514/546; 514/547
(58) Field of Search .................................. 514/532, 533, 514/546, 547, 548

(56) References Cited

U.S. PATENT DOCUMENTS

| | | |
|---|---|---|
| 2,527,602 | 10/1950 | Wall . |
| 3,206,316 | 9/1965 | Klaui . |
| 3,523,138 | 8/1970 | Grant . |
| 3,558,712 | 1/1971 | Surmatis et al. . |
| 3,661,997 | 5/1972 | Surmatis et al. . |
| 3,989,757 | 11/1976 | Surmatis et al. . |
| 3,997,679 | 12/1976 | Salkin . |
| 4,048,203 | 9/1977 | Philip . |
| 4,851,339 | 7/1989 | Hills . |
| 4,929,774 | 5/1990 | Fukamachi et al. . |
| 5,019,668 | 5/1991 | Keat et al. . |
| 5,157,132 | 10/1992 | Tan et al. . |
| 5,180,747 | 1/1993 | Matsuda et al. . |
| 5,290,605 | 3/1994 | Shapira . |
| 5,382,714 | 1/1995 | Khachik . |
| 5,523,494 | 6/1996 | Torres-Cardona et al. . |
| 5,602,286 | 2/1997 | Muralidhara . |
| 5,607,707 | 3/1997 | Ford et al. . |
| 5,643,623 | 7/1997 | Schmitz et al. . |
| 5,648,564 | 7/1997 | Ausich et al. . |
| 5,705,180 | 1/1998 | Schlipalius . |
| 5,712,311 | 1/1998 | Soudant et al. . |
| 5,773,026 | 6/1998 | Schlipalius . |
| 5,780,693 | 7/1998 | Bernhard et al. . |
| 5,804,168 | 9/1998 | Murad . |
| 5,834,044 | 11/1998 | Schmitz et al. . |
| 5,863,953 | 1/1999 | Lueddecke et al. . |
| 5,871,766 | 2/1999 | Hennekens . |
| 5,876,782 | 3/1999 | Sas et al. . |
| 5,886,053 | 3/1999 | Schmutzler et al. . |
| 5,891,907 | 4/1999 | Kolter et al. . |

(List continued on next page.)

FOREIGN PATENT DOCUMENTS

| | | |
|---|---|---|
| WO 93/04598 | 3/1993 | (WO) . |
| WO 95/27483 | 10/1995 | (WO) . |

OTHER PUBLICATIONS

Quackenbush et al., Vitamins and Other Nutrients. Carotenoids in Marigold Petals, J.A.O.A.C. 55(3):617–621, (1972).

J T. Landrum et al., A One Year Study of the Macular Pigment The Effect of 150 Days of a Lutein Supplement, Exp. Eye Res. 65:57–62 (1997).

T. Philip et al., Nature of Lutein Acylation in Marigold (Tagetes Erecta) Flowers, J. Food Sci. 40:1089–1090 (1975).

A.U. Alam et al., Fatty Acid Composition of the Xanthophyll Esters of Tagetes Erecta Petals, Lipids 3(2):183–184 (1967).

J.D.L. Rivas, Raversed–phase High–Performance Liquid Chromatographic Separation of Lutein and Lutein Fatty Acid Esters from Marigold Flower Petral Powder, J. Chrom. 464(2):442–447 (1989).

Straub, Key to Carotenoids, at 63–63, 98, 141–42 (2d ed. 1987).

Mangels, et al., Carotenoid Content of Fruits and Vegetables: An Evaluation of Analytic Data, J. Am. Diet. Assoc. 93(3):284–296 (1993).

Kaplan, et al., Carotenoid Composition, Concentrations, and Relationships in Various Human Organs, Clin. Physiol. Biochem. 8:1–10 (1990).

Seddon, et al., Dietary Carotenoids, Vitamins A, C, and E and Age–Related Macular Degeneration, JAMA 272 (18):1413–1410 (1994).

Natural Colors with the Power to Protect, Quest International, The Netherlands, pp. 1–4.

Landrum, et al., The Macular Pigment: A Possible Role in Protection from Age–Related Macular Degeneration, Adv. Pharm. 38:537–556 (1997).

Guenthner et al., Pigmentation of Egg Yolks by Xanthophylls from Corn, Marigold, Alfalfa and Synthetic Sources, Poultry Sci.: 52:1787–1798 (1973).

The Merck Index at 1120, 8th ed., (1968).

Anticancer Research 16:3689–3694, Effects of Lutein from Marigold Extract on Immunity and Growth of Mammary Tumors in Mice (1996), p. 3690.

(List continued on next page.)

*Primary Examiner*—Deborah Carr
(74) *Attorney, Agent, or Firm*—John E. Drach; Aaron R. Ettelman

(57) ABSTRACT

The present invention provides an antioxidant carotenoid composition substantially free of lutein comprising lutein esters. This antioxidant composition may readily be formulated into products for administration to humans to provide protection from the harmful effects of free radicals. The invention also provides a method of preventing or inhibiting the harmful effects of free radicals by administering an effective amount of an antioxidant carotenoid composition substantially free of lutein comprising lutein esters.

39 Claims, No Drawings

U.S. PATENT DOCUMENTS

| | | |
|---|---|---|
| 5,895,652 | 4/1999 | Giampapa . |
| 5,895,659 | 4/1999 | Lueddecke et al. . |
| 8,847,238 | 12/1998 | Muralidhara . |

OTHER PUBLICATIONS

Khachik, et al., Separation and Identification of Carotenoids and Carotenol Fatty Acid Esters in Some Squash Products by Liquid Chromatography. 1. Quantification of Carotenoids and Related Esters by HPLC, J. Agr. Food Chem. 36:929–937 (1986).

Hammond, Jr., et al., Dietary Modification of Human Macular Pigment Density Investigative Optithal. & Visual Sci. 38(9):1795–891 (1997).

Karrer et al., Extraction from Petals of Tagetes Patula L. Compositae, Helv. Chim. Acta 30:531 (1947).

Derwent Patent Abstract (WPI) No. 97–470453/199743.

Derwent Patent Abstract (WPI) No. 97–036630/199704.

Derwent Patent Abstract (WPI) No. 96–167352/199617.

Derwent Patent Abstract (WPI) No. 97–480954/199745.

LUTEIN ESTERS HAVING HIGH BIOAVAILABILITY

CROSS-REFERENCE TO RELATED APPLICATIONS

This application claims priority under 35 U.S.C. §120, and is a continuation of U.S. patent application Ser. No. 09/054,346, filed Apr. 2, 1998 (now abandoned), which in turn claims priority under 35 U.S.C. §119(e) of U.S. provisional patent application No. 60/042,697, filed Apr. 4, 1997 (now expired), the entire disclosures of which are incorporated herein by reference.

BACKGROUND OF THE INVENTION

1. Field of the Invention

This invention relates to an antioxidant carotenoid composition substantially free of lutein comprising a lutein ester having beneficial antioxidant properties and high bioavailability. This lutein ester composition may be used in antioxidant compositions or preparations that can be administered to humans to provide protection from the harmful, health-damaging effects of free radicals on various body tissues.

2. Background

Carotenoids are phytonutrients, the nutritional elements that give fruits and vegetables their orange, yellow, and red colors. Green leafy vegetables are also high in carotenoids, but the color is masked by chlorophyll. Although β-carotene may be the best-known and most abundant dietary carotenoid, approximately 500 carotenoids, including lutein, lycopene, cryptoxanthin and zeaxanthin, have been identified. Carotenoids provide health benefits, primarily because of their antioxidant properties. Such benefits include protecting the body from skin, eye, liver, and lung damage, and certain forms of cancer.

Recent scientific studies have provided evidence that antioxidants are capable of protecting healthy cells from free radical damage. Free radicals are unstable chemicals formed in the body during metabolism and from exposure to environmental sources, such as air pollution, cigarette smoke, and dietary fats. When there is an excessive number of free radicals in the body, free radicals can attack healthy cells and can contribute to a number of degenerative diseases, such as cancer.

Free radicals have been linked to numerous diseases and health conditions. Conditions associated with free radicals and affecting multiple organs include: inflammatory-immune injury (idiopathic and membranous glomerulonephritis, vasculitis caused by hepatitis B virus and intravenous drug use, autoimmune diseases); ischemia-reflow states; drug- and toxin-induced reactions; iron overload (idiopathic hemochromatosis, dietary iron overload, thalassemia, and other chronic anemias); nutritional deficiencies (Kwashiorkor, Vitamin E deficiency); alcohol damage; radiation injury; aging (premature aging disorders, age-related immunodeficiency); cancer; and amyloid diseases. Conditions relating to specific organs or tissues and associated with free radicals include: erythrocytes, lead poisoning, protoporphyrin photo-oxidation, malaria, sickle-cell anemia, favism, Fanconi anemia); lung (effects of tobacco smoking, emphysema, hyperoxia, bronchopulmonary dysplasia, oxidant pollutants, acute respiratory distress syndrome, mineral dust pneumoconiosis, bleomycin toxicity, paraquat toxicity); rheumatoic arthritis and other joint abnormalities; heart and cardiovascular (alcohol cardiomyopathy, Keshan diseases (selenium deficiency), atherosclerosis, doxorubicin toxicity); kidney (nephrotic antiglomerular basement membrane disease, aminoglycoside nephrotoxicity, heavy metal nephrotoxicity, renal graft rejection); gastrointestinal tract (endotoxin liver injury, carbon tetrachloride liver injury, diabetogenic action of alloxan, free fatty-acid induced pancreatitis, nonsteroidal anti-inflammatory drug-induced lesions); brain (hyperbaric oxygen, neurotoxins, senile dementia, Parkinson's disease (MPTP), hypertensive cerebrovascular injury, cerebral trauma, allergic encephalomyelitis and other demyelinating diseases, ataxia-telangiectasia syndrome, potentiation of traumatic injury, aluminum overload, abetalipoproteinemia); eye (cataractogenisis, ocular hemorrhage, degenerative retinal damage, premature retinopathy, photic retinopathy); and skin (solar radiation, thermal injury, porphyria, contact dermatitis, photosensitive dyes, Bloom syndrome).

Antioxidants quench free radicals before they have a chance to attack healthy cells. Antioxidants have been shown in the majority of studies to lower the risk for certain cancers, such as lung, stomach, cervix, breast, bladder, and oral cancers. Other health benefits include protection against heart diseases, cataracts, and age-related macular degeneration. While free radicals can cause or complicate many diseases, including cancer, arthritis, cataracts, and heart diseases, antioxidants can help protect the body from these chronic disorders. They also enhance the body's immune system.

One of the most common carotenoid compounds, lutein (also referred to as vegetable lutein or vegetable luteol, xanthophyll, or β,ε-carotene-3,3'-diol) has the following formula (I):

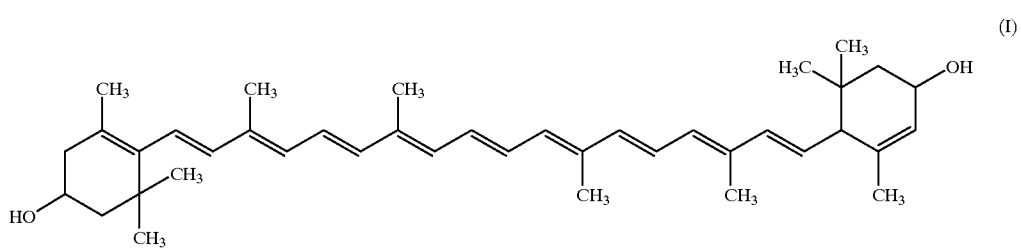

A carotenoid alcohol, lutein is found naturally in many sources, such as egg yolk, nettles, algae, and the petals of many yellow flowers. Lutein is also one of the major constituents of green vegetables and fruits such as broccoli, green beans, green peas, Brussels sprouts, cabbage, kale, spinach, lettuce, kiwi, and honeydew. Lutein is also present in many plants in the form of mono- or diesters. For example, lutein dipalmitate, also known as helenien or Adaptinol, is present in *Helenium autumnale L., Compositae,* and other flowers. Lutein can be isolated from these materials using procedures well-known in the art. See, e.g., Karrer et al. (*Helv. Chim. Acta* 30:531 (1947)).

Lutein in its free or unesterified form is also found in the human bloodstream, presumably as a result of dietary absorption of lutein in food. Because of this and concerns about the suitability of lutein esters for human consumption, prior art methods of increasing plasma lutein concentrations have emphasized dietary supplements containing free lutein. See, U.S. Pat. No. 5,382,714.

SUMMARY OF THE INVENTION

The inventors have surprisingly found that lutein esters have a bioavailability as high or higher than free lutein. The present invention thus provides a natural antioxidant carotenoid composition substantially free of free lutein (hereinafter "lutein") comprising a lutein ester. The composition of the present invention is a natural antioxidant which may readily be formulated into oral products for administration to humans to provide protection from the harmful effects of free radicals. Accordingly, the present invention also provides a method of preventing or inhibiting the harmful effects of free radicals by administering an effective amount of an antioxidant carotenoid composition substantially free of lutein comprising a lutein ester.

With the foregoing and other objects, advantages and features of the invention that will become hereinafter apparent, the nature of the invention may be more clearly understood by reference to the following detailed description of the preferred embodiments of the invention and to the appended claims.

DETAILED DESCRIPTION OF THE PREFERRED EMBODIMENTS OF THE INVENTION

Accordingly, the present invention provides a composition with beneficial antioxidant properties, comprising lutein esters. Such a composition may be formulated as a stable, natural product. The lutein esters or esters which comprise the antioxidant composition of the present invention provide a natural source of carotenoid antioxidants and can be any lutein ester of the formula (II):

caproic, caprylic, capric, lauric, myristic, palmitic, stearic, and oleic acids. Particularly preferred are lauric, palmitic, stearic, oleic, and myristic acids.

Accordingly, the lutein ester of the present invention can be any mono- or diester, homogeneous or mixed. Suitable esters therefore include lutein mono- or diformate, mono- or diacetate, mono- or dipropionate, mono- or dibutyrate, mono- or divalerate, mono- or dicaproate, mono- or dicaprylate, mono- or dicaprate, mono- or dilaurate, mono- or dimyristate, mono- or dipalmitate, mono- or distearate, and mono- or dioleate, as well as mixed esters such as lutein myristate-palmitate and palmitate-stearate. Preferably the ester of the composition of the invention is a mixture of 50% to 60% by weight lutein dipalmitate, 30% to 40% by weight of lutein dimyristate, and 5% to 10% by weight of lutein monomyristate, based on the total weight of lutein esters present in the composition. Particularly preferred is a mixture of 56% by weight lutein dipalmitate, 36% by weight lutein dimyristate, and 8% lutein monomyristate.

Lutein esters for use in the present invention may be readily extracted from plant materials using known methods. In a preferred embodiment, the lutein ester of the invention is derived from the petals of the marigold flower, *Tagetes erecta*. The marigolds *T. grandiflora, T. patula,* and *T. nana* Ehrenkreutz are also suitable sources for the lutein ester. In a typical process, the marigold flowers are harvested, dried, and milled. The milled marigolds are extracted with a food grade solvent. The carotenoid fraction is then concentrated, for example, by solvent removal through vacuum distillation. Alternatively, the lutein ester may be synthesized by any means known in the art to the skilled practitioner, e.g., via esterification from free lutein.

Antioxidant Compositions

The present invention provides a composition substantially free of lutein comprising an effective antioxidant amount of a lutein ester and a physiologically acceptable carrier suitable for oral administration. As usual herein, the term "substantially free of lutein" means that the composition is at least 90% by weight, preferably at least 94% by weight, and more preferably at least 99% by weight of the lutein ester, based on the total carotenoid weight of the composition.

The compositions of the present invention can be made by conventional compounding procedures known in the pharmaceutical art, that is, by mixing the active substances with edible physiologically acceptable, non-toxic, inert, solid, or liquid carriers and/or excipients suitable for systemic admin-

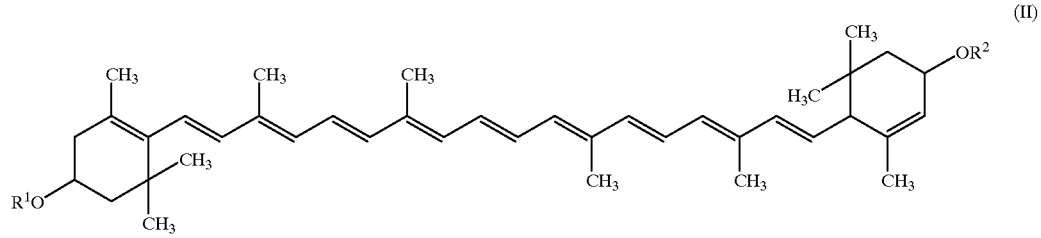

wherein $R^1$ and $R^2$ are the same or different and are H or an acyl residue of a carboxylic acid, provided $R^1$ and $R^2$ are not H simultaneously.

Preferably, $R^1$ and $R^2$ are the residue of a saturated or unsaturated $C_1$ to $C_{22}$ fatty carboxylic acid, more preferably a $C_6$ to $C_{22}$ fatty acid, and even more preferably a $C_{12}$ to $C_{22}$ fatty acid. Suitable preferred acids forming the residue of $R^1$ or $R^2$ include formic, acetic, propionic, butyric, valeric, istration and conventionally used in oral dosage forms. Preferably, carriers for use in the present invention will be natural carriers, such as edible oils. The edible oil may be a vegetable oil such as avocado, coconut, corn, grape seed, palm, peanut, olive, sesame, soya, rapeseed, or walnut oil or any other edible vegetable oil or mixture of one or more of these oils. Additionally, edible, non-toxic pharmaceutically acceptable stabilizers usually used as stabilizers in oral dosage forms or edible, non-toxic salts thereof can be included in the compositions. Preferably, the stabilizer will be beeswax or silica. All the above carriers, excipients and stabilizers are intended to include only those suitable for oral administration and all are conventional and known to the pharmaceutical art.

Preferably, the compositions of the present invention comprise at least 4% by weight of the lutein ester, more preferably at least 5% by weight of the lutein ester, and more preferably at least 15% by weight of the lutein ester, although the present invention contemplates compositions comprising at least 25%, 30%, 40%, and even 50% by weight of the lutein ester, based on the total weight of the composition.

The compositions for oral administration may be in the form of tablets, including sustained release forms, lozenges, chewing gum, and capsules. The soft gelatin capsule dosage form is most preferred. These dosage forms may be prepared by those skilled in the art in accordance with known techniques in the art, for example, as described in *Remington's Pharmaceutical Sciences,* 17th Edition (1985), Mack Publishing Co., Easton, Pa.

According to the present invention, the patient ingests the composition preferably daily to obtain the benefit of the administration of the lutein esters. The dosage of the antioxidant composition of the present invention administered to a patient will vary depending upon several factors, including, but not limited to, the age and weight of the patient, the general health of the patient, the severity of the symptoms, and the like. The typical dosage form will contain 0.5 mg to 50 mg, preferably 0.5 mg to 30 mg of lutein ester.

Method of Treatment

The present invention also includes a method for preventing or inhibiting the harmful effects of free radicals comprising administering to a mammal, including a human, in need of such treatment an effective amount of the carotenoid antioxidant composition of the present invention, comprising an effective amount of a lutein ester to prevent or inhibit oxidation by free radicals. This method may be practiced by administration of the natural antioxidant composition by itself or in combination with other active ingredients, including other antioxidants, and/or therapeutic agents in a pharmaceutical composition. Other therapeutic agents suitable for use herein are any compatible drugs that are effective by the same or other mechanisms for the intended purpose, or drugs that are complementary to those of the present agents. Examples include carotenoids (e.g., beta carotene derived from *Dunaliella salina*) and vitamins (e.g., natural tocopherols derived from soybean oil, such as d-α-tocopherol), among others. Preferably, the compatible compounds will be natural antioxidants.

The compounds utilized in combination therapy may be administered simultaneously, in either separate or combined formulations, or at different times than the present compounds, e.g., sequentially, such that a combined effect is achieved. The amounts and regime of administration will be adjusted by the practitioner, by preferably initially lowering their standard doses and then titrating the results obtained. A typical regimen according to the invention would result in daily administration of 0.5 mg to 50 mg of lutein ester.

The following examples are presented in order to more fully illustrate the preferred embodiments of the invention. They should in no way be construed, however, as limiting the broad scope of the invention.

EXAMPLE 1

The objective of this experiment is to determine whether there is a difference between the bioavailability upon chronic dosing lutein and its diester.

Experimental Design

Experiments were performed as a randomized crossover design with a washout period between interventions. The first 24-hr period of each supplement dosing period constituted the acute dosing period. Subjects were fed a low carotenoid diet of solid foods during this 24-hr period. Following a three week washout period, subjects were then crossed over to the alternate supplement for a second study period. Subjects consumed their usual diets during the study period and were counseled to consume modest amounts of carotenoid-containing foods. Randomization was stratified by age, sex, and beginning serum lutein levels.

Subjects

Eighteen healthy, non-smoking subjects (10 men and 8 women) ages 18–55 were recruited for this experiment. The body mass index (BMI) of the subjects ranged from 21–30. Subjects suffered from no chronic diseases or gastrointestinal disturbances, were taking no prescription or over-the-counter drugs during the study, no vitamin or mineral supplements, with baseline serum lutein levels not greater than 20 $\mu$g/dl.

Blood Sampling Regimen

Subjects reported to the laboratory on the morning of the first day of the study in a fasting state. A butterfly catheter was inserted into an arm vein and 3 cc of blood was drawn to permit establishment of baseline values. Single doses of lutein and lutein diester at 0.5 or 0.65 $\mu$mol/kg body weight were consumed with a glass of water followed by a low carotenoid study breakfast containing 30% of kcal from fat and constituting 20% of the subject's energy needs for the day. Further 3 cc blood samples were drawn at 0, 2, 4, 6, 8, 10, 12, and 16 hours through the catheter. The patency of the catheter was maintained with heparin. Subjects were then sent home (catheter removed) with instructions to avoid the consumption of any food or beverage other than water. They returned to the laboratory the next morning and another 3 cc blood sample was taken. Subjects were then provided with a low carotenoid breakfast and lunch, then returned for the 34 hour blood draw. Remaining blood draws were obtained at 72, 120, 240, and 408 hours after baseline. The study was repeated with the alternate formulation with a 3 wk washout between studies. During each study the participants followed a low carotenoid diet. Serum lutein concentrations from hours 0 through 408 were measured by HPLC and areas under the serum concentration time curve (AUC) were calculated to determine differences in bioavailability of lutein and lutein diester.

Results

The mean AUCs for lutein and lutein diester were 1301±1080 and 2103±2036, respectively (p=0.07). Mean time to peak for lutein was 29.6 hours and for lutein diester was 26.5 hours. Baseline values were reached by 408 hours. The lutein diester formulation had a slower disappearance slope producing a longer serum residence time. Lutein diester showed a trend toward greater bioavailability suggesting that the human gut is very efficient in cleaving esters of lutein and therefore esterified lutein in food is equally bioavailable.

While the invention has been described and illustrated herein by references to various specific material, procedures and examples, it is understood that the invention is not restricted to the particular material, combinations of material, and procedures selected for that purpose. Numerous variations of such details can be implied and will be appreciated by those skilled in the art.

What is claimed is:

1. A method of preventing or inhibiting free radical oxidation in a mammal; said method comprising:

(i) providing a composition comprising at least one lutein ester of the formula (II)

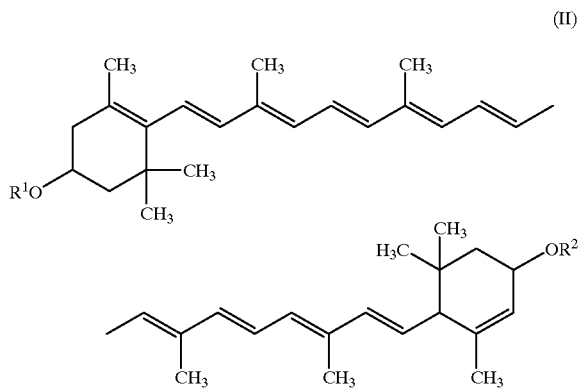

wherein $R^1$ and $R^2$ each independently represent a hydrogen atom or an acyl residue of a carboxylic acid, wherein at least one of $R^1$ and $R^2$ represents an acyl residue of a carboxylic acid; and (ii) administering an antioxidant-effective amount of the composition to a mammal.

2. The method according to claim 1, wherein the at least one lutein ester is present in an amount of at least about 4% by weight, based on the total weight of the composition.

3. The method it according to claim 1, wherein the at least one lutein ester is present in an amount of at least about 5% by weight, based on the total weight of the composition.

4. The method according to claim 1, wherein the at least one lutein ester is present in an amount of at least about 15% by weight, based on the total weight of the composition.

5. The method according to claim 1, wherein the at least one lutein ester is present in an amount of at least about 25% by weight, based on the total weight of the composition.

6. The method according to claim 1, wherein the at least one lutein ester is present in an amount of at least about 30% by weight, based on the total weight of the composition.

7. The method according to claim 1, wherein the at least one lutein ester is present in an amount of at least about 40% by weight, based on the total weight of the composition.

8. The method according to claim 1, wherein the at least one lutein ester is present in an amount of at least about 50% by weight, based on the total weight of the composition.

9. The method according to claim 1, wherein the composition is substantially free of lutein.

10. The method according to claim 1, wherein the at least one lutein ester is present in an amount of at least about 90% by weight, based on the total carotenoid weight of the composition.

11. The method according to claim 1, wherein the at least one lutein ester is present in an amount of at least about 94% by weight, based on the total carotenoid weight of the composition.

12. The method according to claim 1, wherein the at least one lutein ester is present in an amount of at least about 99% by weight, based on the total carotenoid weight of the composition.

13. The method according to claim 1, wherein $R^1$ and $R^2$ each independently represent a hydrogen atom or an acyl residue of a carboxylic acid having from 1 to 22 carbon atoms.

14. The method according to claim 1, wherein $R^1$ and $R^2$ each independently represent a hydrogen atom or an acyl residue of a carboxylic acid having from 6 to 22 carbon atoms.

15. The method according to claim 1, wherein $R^1$ and $R^2$ each independently represent a hydrogen atom or an acyl residue of a carboxylic acid having from 12 to 22 carbon atoms.

16. The method according to claim 1, wherein $R^1$ and $R^2$ each independently represent a hydrogen atom or an acyl residue of a carboxylic acid selected from the group consisting of formic, acetic, propionic, butyric, valeric, caproic, caprylic, capric, lauric, myristic, palmitic, stearic, and oleic acids.

17. The method according to claim 1, wherein $R^1$ and $^2$ each independently represent a hydrogen atom or an acyl residue of a carboxylic acid selected from the group consisting of lauric, myristic, palmitic, stearic, and oleic acids.

18. The method according to claim 1, wherein the composition comprises lutein monomyristate, lutein dimyristate and lutein dipalmitate.

19. The method according to claim 18, wherein the lutein monomyristate is present in an amount of from about 5% to about 10% by weight, the lutein dimyristate is present in an amount of from about 30% to about 40% by weight and the lutein dipalmitate is present in an amount of from about 50% to about 60% by weight, based upon the total weight of lutein esters.

20. The method according to claim 18, wherein the lutein monomyristate is present in an amount of about 8% by weight, the lutein dimyristate is present in an amount of about 36% by weight and the lutein dipalmitate is present in an amount of about 56% by weight, based upon the total weight of lutein esters.

21. The method according to claim 1, wherein the composition is administered in a dosage of from about 0.5 mg to about 50 mg of the at least one lutein ester.

22. The method according to claim 1, wherein the composition further comprises a pharmaceutically acceptable carrier.

23. A method of preventing or inhibiting free radical oxidation in a mammal, said method comprising:
(i) providing a composition lutein monomyristate, lutein dimyristate and lutein dipalmitate, wherein the lutein monomyristate is present in an amount from about 5% to about 10% by weight, the lutein dimyristate is present in an amount of from about 30% to about 40% by weight and the lutein dipalmitate is present in an amount of from about 50% to about 60% by weight, based upon the total weight of lutein esters, and a physiologically acceptable carrier, wherein the lutein esters are present in an least about 4% by weight, based on the total weight of the composition, and wherein the lutein esters are present in an amount of at least about 90% by weight, based on the total carotenoid weight of the composition; and
(ii) administering an antioxidant-effective amount of the composition to a mammal.

24. The method according to claim 23, wherein the lutein esters are present in an amount of at least about 5% by weight, based on the total weight of the composition.

25. The method according to claim 23, wherein the lutein esters are present in an amount of at least about 5% by weight, based on the total weight of the composition.

26. The method according to claim 23, wherein the lutein esters are present in an amount of at least about 25% by weight, based on the total weight of the composition.

27. The method according to claim 23, wherein the lutein esters are present in an amount of at least about 30% by weight, based on the total weight of the composition.

28. The method according to claim 23, wherein the lutein esters are present in an amount of at least about 40% by weight, based on the total weight of the composition.

29. The method according to claim 23, wherein the lutein esters are present in an amount of at least about 50% by weight, based on the total weight of the composition.

30. The method according to claim 23, wherein the lutein esters are present in an amount of at least about 94% by weight, based on the total carotenoid weight of the composition.

31. The method according to claim 23, wherein the lutein esters are present in an amount of at least about 99% by weight, based on the total carotenoid weight of the composition.

32. The method according o claim 23, wherein the lutein esters are present in an amount of at least about 15% by weight, based on the total weight of the composition, and wherein the lutein esters are present in an amount of at least about 94% by weight, based on the total carotenoid weight of the composition.

33. The method according to claim 23, wherein the lutein esters are present in an amount of at least about 30% by weight, based on the total weight of the composition, and wherein the lutein esters are present in an amount of at least about 94% by weight, based on the total carotenoid weight of the composition.

34. The method according to claim 23, wherein the lutein esters are present in an amount of at least about 40% by weight, based on the total weight of the composition, and wherein the lutein esters are present in an amount of at least about 94% by weight, by on the total carotenoid weight of the composition.

35. The method according to claim 23, wherein the lutein esters are present in an amount of at least about 50% by weight, based on the total weight of the composition, and wherein the lutein esters are present in an amount of at least about 94% by weight, based on the total carotenoid weight of the composition.

36. The method according to claim 23, wherein the lutein esters are present in an amount of a least about 15% by weight, based on the total weight of the composition, and wherein the lutein esters are present in an amount of at least about 99% by weight, based on the total carotenoid weight of the composition.

37. The method according to claim 23, wherein the lutein esters are present in an amount of a least about 30% by weight, based on the total weight of the composition, and wherein the lutein esters are present in an amount of at least about 99% by weight, based on the total carotenoid weight of the composition.

38. The method according to claim 23, wherein the lutein esters are present in an amount of at least about 40% by weight, based on the total weight of the composition, and wherein the lutein esters are present in an amount of at least about 99% by weight, based on the total carotenoid weight of the composition.

39. The method according to claim 23, wherein the lutein esters are present in an amount of at least about 50% by weight, based on the total weight of the composition, and wherein the lutein esters are present in an amount of at least about 99% by weight, based on the total carotenoid weight of the composition.

\* \* \* \* \*